(12) United States Patent
Kadaboina et al.

(10) Patent No.: US 9,376,394 B2
(45) Date of Patent: Jun. 28, 2016

(54) PREPARATION OF BENDAMUSTINE AND ITS SALTS

(75) Inventors: Rajasekhar Kadaboina, Andhra Pradesh (IN); Veerender Murki, Andhra Pradesh (IN); Venkat Rao Badisa, Andhra Pradesh (IN); Nageshwar Gunda, Andhra Pradesh (IN)

(73) Assignees: DR. REDDY'S LABORATORIES LTD., Hyderabad (IN); DR. REDDY'S LABORATORIES, INC., Bridgewater, NJ (US)

( * ) Notice: Subject to any disclaimer, the term of this patent is extended or adjusted under 35 U.S.C. 154(b) by 822 days.

(21) Appl. No.: 13/517,908

(22) PCT Filed: Dec. 22, 2010

(86) PCT No.: PCT/US2010/061782
§ 371 (c)(1),
(2), (4) Date: Mar. 5, 2013

(87) PCT Pub. No.: WO2011/079193
PCT Pub. Date: Jun. 30, 2011

(65) Prior Publication Data
US 2013/0158273 A1    Jun. 20, 2013

Related U.S. Application Data

(60) Provisional application No. 61/320,353, filed on Apr. 2, 2010.

(30) Foreign Application Priority Data

Dec. 23, 2009 (IN) ............................ 3167/CHE/2009
Sep. 15, 2010 (IN) ............................ 2706/CHE/2010

(51) Int. Cl.
*C07D 235/16* (2006.01)

(52) U.S. Cl.
CPC ................................. *C07D 235/16* (2013.01)

(58) Field of Classification Search
USPC ........................................................ 548/310.1
See application file for complete search history.

(56) References Cited

U.S. PATENT DOCUMENTS

2,969,364 A * 1/1961 Lyttle ............................ 544/311
8,076,366 B2 * 12/2011 Courvoisier et al. ......... 514/394
2004/0087813 A1 † 5/2004 Springer

FOREIGN PATENT DOCUMENTS

| CN | 101691359 A | 4/2010 |
| DE | 34727 | 12/1964 |
| IN | 3167/CHE/2009 † | 1/2013 |
| WO | WO-2005/113498 A1 * | 12/2005 |
| WO | 2009/120386 A2 | 10/2009 |
| WO | 2010/042568 A1 | 4/2010 |
| WO | WO-2010/042568 A1 * | 4/2010 |

OTHER PUBLICATIONS

Li-mei Gao et al., Zhongguo Xinyao Zazhi, 2007, 16(23), pp. 1960, 1961 and 1970.*
An English translation of Li-mei Gao et al., Zhongguo Xinyao Zazhi, 2007, 16(23), pp. 1960, 1961 and 1970.*
International Search Report dated, Oct. 4, 2011 for corresponding International Patent Application No. PCT/US2010/061782.
21 (Anonymous), "Process for Preparing 4-[5-[Bis(2-Chloroethyl)Amino]-1-Methylbenzimidazol-2-Yl] Butanoic Acid Intermediate", IP.com Journal, Jul. 13, 2009, vol. 9-issue No. 7B.
Anonymous Author, Process for Preparing 4-[5- [Bis(2-Chloroethyl)Amino]-1-Methylbenimidazol-2-Yl]Butanoic Acid Intermediate, 3 pages, Jul. 13, 2009, IP.COM Prior Art Database Disclosure, Disclosure No. IPCOM000185126D, Internet.†

* cited by examiner
† cited by third party

*Primary Examiner* — Laura L Stockton
(74) *Attorney, Agent, or Firm* — Pergament & Cepeda LLP; Milagros A. Cepeda; Edward D. Pergament

(57) ABSTRACT

The present application relate to processes for the preparation of bendamustine and its pharmaceutically acceptable salts.

11 Claims, 3 Drawing Sheets

PREPARATION OF BENDAMUSTINE AND ITS SALTS

This application is a National Stage Application under 35 U.S.C. 371 of PCT International Application No. PCT/US2010/061782, filed Dec. 22, 2010, which is hereby incorporated by reference in its entirety, which PCT/US2010/061782 application claims priority to Indian Provisional Applications 3167/CHE/2009, filed on Dec. 23, 2009; 2706/CHE/2010, filed on Sep. 15, 2010; and U.S. Provisional Application No. 61/320,353, filed on Apr. 2, 2010.

INTRODUCTION

Aspects of the present application relate to processes for the preparation of bendamustine and its pharmaceutically acceptable salts.

Bendamustine hydrochloride has chemical names: (4-{5-[bis(2-chloroethyl)amino]-1-methyl-2-benzimidazolyl}-butyric acid hydrochloride or 1H-benzimidazole-2-butanoic acid, 5-[bis(2-chloroethyl)amino]-1-methyl-,monohydrochloride and is represented by structural formula (I).

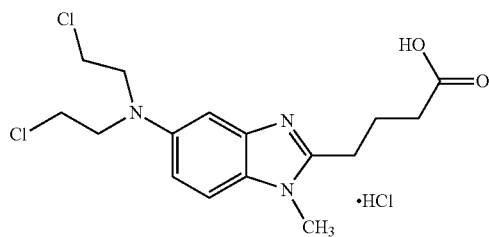

(I)

Bendamustine hydrochloride is a benzimidazole analog and is sold by Cephalon, Inc. as TREANDA® in the form of a sterile non-pyrogenic white to off-white lyophilized powder in a single use vial, for the treatment of chronic lymphocytic leukemia.

Ozegowski et al., in Zbl. Pharma. 110, (1971) Heft 10, 1013-1019, discloses a process for the preparation of bendamustine hydrochloride monohydrate. German Democratic Republic Patent No. 34727 discloses a process for the preparation of ω-[5-bis(β-chloroethyl)amino-benzimidazolyl-(2)]alkane carboxylic acids substituted in the 1-position.

Li-Mei et al., in Zhongguo Xinyao Zazhi (2007), 16(23), 1960-1961, 1970 disclose a process for the preparation of bendamustine hydrochloride monohydrate, which involves reacting [1-methyl-2-(4'-ethyl butyrate)-5-amino]-1H-benzimidazole with ethylene oxide in the presence of water, sodium acetate and acetic acid, by maintaining at 5° C. for 5 hours and overnight at 20° C. to give (4-{5-[bis-(2-hydroxyethyl)-amino]-1-methyl-1H-benzimidazol-2-yl}-butyric acid ethyl ester as a jelly mass, which on chlorination using thionyl chloride in chloroform and in situ hydrolysis with concentrated HCl at 90-95° C. gave bendamustine hydrochloride. It also discloses a process for the recrystallization of bendamustine hydrochloride from water and the product obtained is a monohydrate with a melting point of 148-151° C.

R. Gust et al., in Monatshefte fur Chemie (1997), 128, 291-299 disclose that the known process synthesis of bendamustine has been performed by an eleven step sequence starting from 2,4-dinitrochlorobenzene, and the crucial conversions are the chlorination of ethyl 4-(6-bis(2-hydroxyethylamino)-3-methylbenzimidazoylbutyrate (dihydroxy ester) with $SOCl_2$, affording ethyl 4-(6-bis(2-chloroethyl)amino-3-methylbenzimidazol-2-ylbutyrate (dichloro ester) and the subsequent ester cleavage with HCl to obtain 4-(6-bis(2-chloroethyl)-amino-3-methylbenzimidazol-2-ylbutyric acid (bendamustine). Under the reaction conditions employed, bendamustine hydrolyzes in small amounts to form the hydroxychloro (HP1) and dihydroxy (HP2) derivatives.

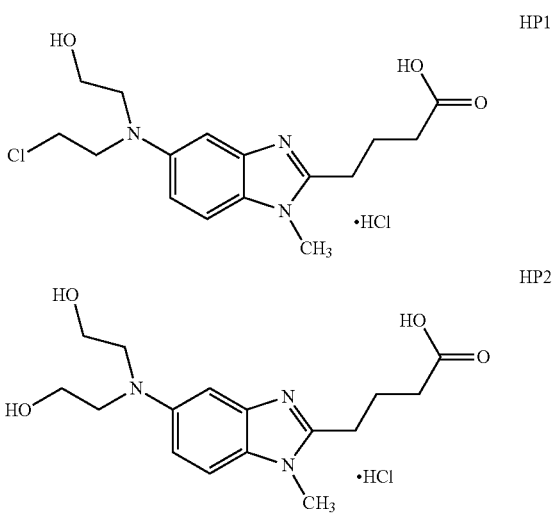

IP.com Journal 2009, 9(7B), 21 discloses a process for the preparation of ethyl-4-[5-[bis(2-hydroxyethyl)amino]-1-methylbenzimidazol-2-yl]butanoate wherein ethyl-4-(5-amino-1-methyl-1H-benzo[d]imidazol-2-yl)butanoate is reacted with 2-halo ethanol in the presence of an inorganic base selected from the group consisting potassium carbonate, potassium bicarbonate, sodium carbonate, and sodium bicarbonate.

The various known processes involve the use of ethylene oxide in the preparation of bendamustine hydrochloride, which is often not suitable for industrial scale processes due to difficulty in handling ethylene oxide, since it is shipped as a refrigerated liquid. Further, ethylene oxide is known to cause several health hazards as it is toxic by inhalation with an $LD_{50}$ of 330 mg/Kg and is classified as potentially carcinogenic to humans by the International Agency for Research on Cancer. Further, the known processes involve the use of strongly acidic conditions and high temperatures for the hydrolysis, thereby resulting in increased levels of various process-related impurities.

International Application Publication No. WO 2009/120386 A2 describes solid forms of bendamustine hydrochloride designated as bendamustine hydrochloride Form 1, bendamustine hydrochloride Form 2, bendamustine hydrochloride Form 3, bendamustine hydrochloride Form 4, amorphous bendamustine hydrochloride or a mixture thereof, processes for their preparation and lyophilized composition comprising the solid forms. According to the disclosure, monohydrate of bendamustine hydrochloride has been prepared previously. See, W. Ozegowski and D. Krebs. The monohydrate has a reported melting point of 152-156° C. which is similar to that of the observed melting point of bendamustine hydrochloride Form 2.

Therefore, there remains a need for improved processes for the preparation of bendamustine hydrochloride, producing high yield and purity, and well-suited for use on an industrial scale. Despite the existence of various polymorphic forms of bendamustine hydrochloride, there exists a need for a simple process for the preparation of the stable form of bendamustine hydrochloride which is amenable to scale up and results in high yield and purity.

SUMMARY OF THE INVENTION

An aspect of the present application provides processes for the preparation of bendamustine hydrochloride, embodiments comprising:

a) reacting a compound of formula (II):

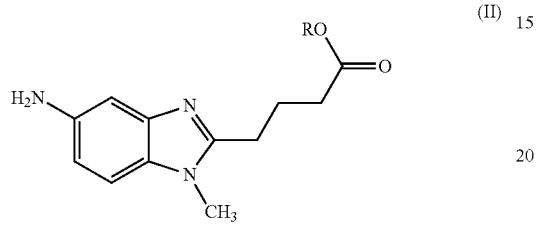

wherein R is a $C_1$-$C_4$ alkyl group, with a 2-haloethanol in the presence of an organic base to give a compound of formula (III);

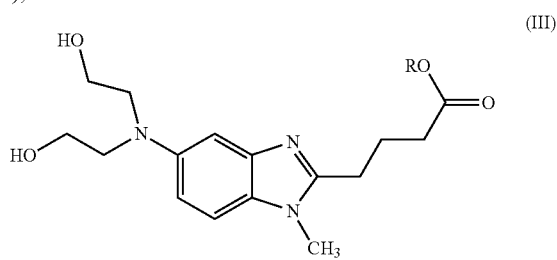

b) reacting the compound of formula (III) with a chlorinating agent to provide a compound of formula (IV); and

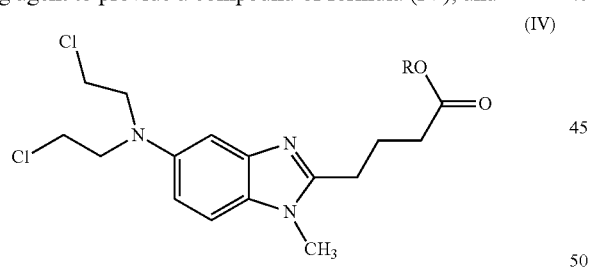

c) hydrolyzing the compound of formula (IV) to give bendamustine hydrochloride.

Another aspect of the present application provides a compound of the formula (IIIa).

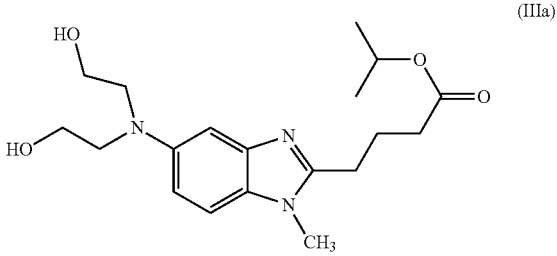 [SMILES: CC(C)OC(=O)CCCc1nc2cc(N(CCO)CCO)ccc2n1C]

Another aspect of the present application provides process for the purification of bendamustine hydrochloride, embodiments comprising:

a) combining bendamustine hydrochloride, aqueous hydrochloric acid, and acetonitrile;

b) heating the mixture of step a) to a temperature of about 35° C. to about 65° C.;

c) cooling the mixture of step b) from about 0° C. to about 35° C.; and d) isolating bendamustine hydrochloride.

DETAILED DESCRIPTION

Figure 1:
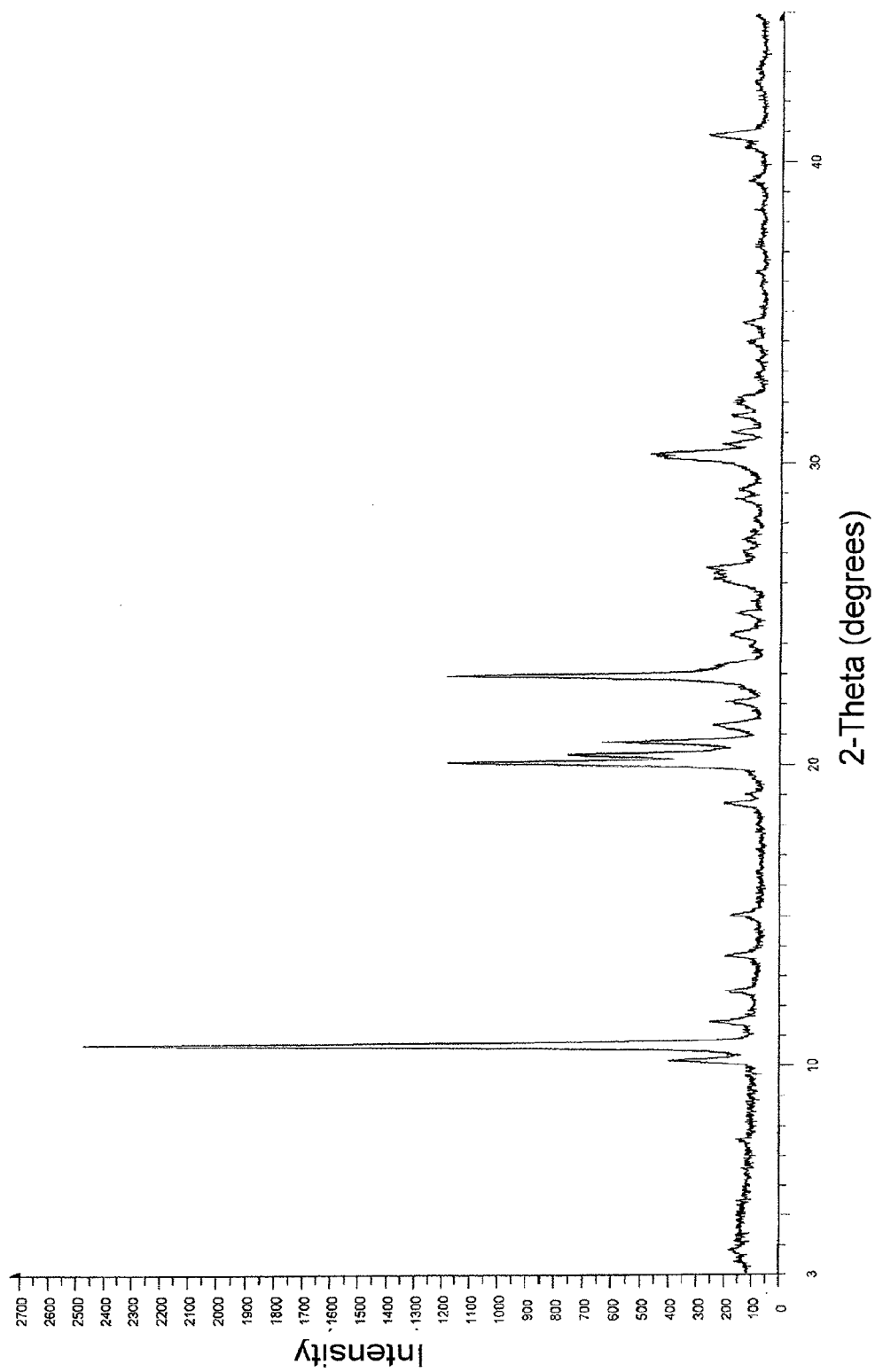
FIG. 1 is an illustrative X-ray powder diffraction pattern of Bendamustine hydrochloride prepared as per Example 5 (Part-A).

Embodiments of the application relate to the preparation of bendamustine hydrochloride. Those skilled in the art will recognize that the processes can easily be modified to prepare other salts of bendamustine.

An aspect of the present application provides processes for the preparation of bendamustine hydrochloride, embodiments comprising:

a) reacting a compound of formula (II):

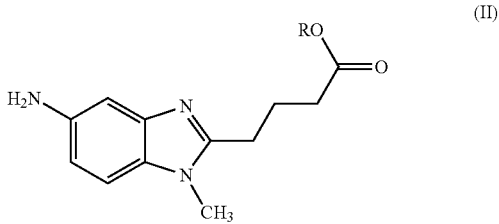

wherein R is a $C_1$-$C_4$ alkyl group, with a 2-haloethanol in the presence of an organic base to give a compound of formula (III);

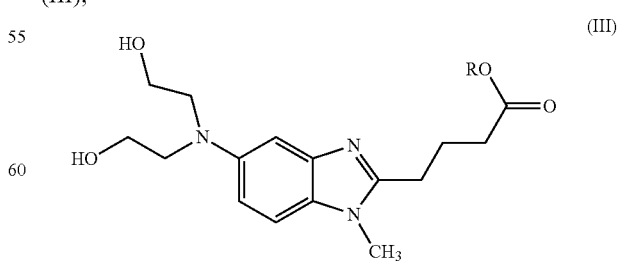

b) reacting the compound of formula (III) with a chlorinating agent to provide a compound of formula (IV); and

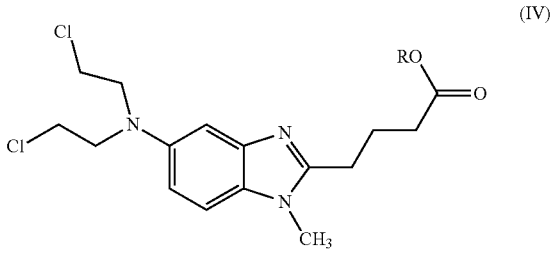

c) hydrolyzing the compound of formula (IV) to give bendamustine hydrochloride.

Steps for this process are separately described below.

Step a) involves reacting a compound of formula (II) with a 2-haloethanol in the presence of an organic base to give a compound of formula (III). The starting compound of formula (II) may be obtained by known processes including the process disclosed by Li-Mei et al. in Zhongguo Xinyao Zazhi (2007), 16(23), 1960-1961, 1970. 2-Haloethanol compounds that may be used in the processes of the present application include 2-chloroethanol, 2-bromoethanol, 2-iodoethanol, or the like. Typical amounts of 2-haloethanol that are used are from about 2 to about 40 molar equivalents, per molar equivalent of compound of formula (II). In embodiments, about 2 to about 12 molar equivalents of 2-haloethanol, per molar equivalent of compound of formula (II), are used. In one embodiment, about 4 molar equivalents of 2-haloethanol, per molar equivalent of compound of formula (II), are used.

Organic bases such as triethylamine, diisopropyl amine, diisopropyl-ethylamine, DABCO, pyridine, lutidine, 4-dimethylaminopyridine, 4-methylmorpholine or the like may be used as the base in step a). In particular embodiments, triethylamine, diisopropylamine, or diisopropyl-ethylamine is used as the base.

In an embodiment, the reaction of step (a) may optionally be carried out in stages, i.e., the 2-haloethanol and the base may be added and reacted in increments.

The inventors of the present application have found that use of an inorganic base, e.g. potassium carbonate, in the above step as per the prior art process hydrolyses the ester group, results in the lower yield, and the product was obtained as a gummy mass. Furthermore, when an inorganic base was used for step a) the purity of the product obtained was found to be not more than 80% by HPLC, with the content 4-(5-(2-hydroxyethylamino)-1-methyl-1H-benzo[d]imidazol-2-yl)butanoic acid ester (Impurity C) being more than 15%.

Impurity C

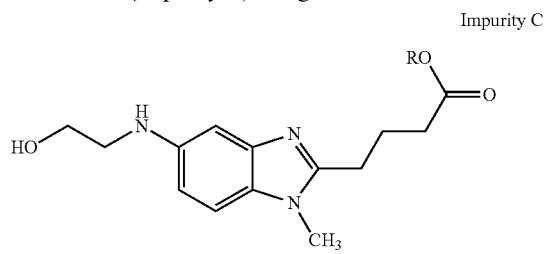

It was surprisingly found that the rate of completion of the reaction was faster in the presence of an organic base and product was obtained in higher yield and a purity of greater than about 95%, with Impurity C present in less than about 0.5% and with minimum amounts of the other undesired side products. In one embodiment the purity of the compound of formula (III) is greater than about 97%.

The reaction of step a) may be carried out in the presence of a solvent. Useful solvents include, without limitation thereto, water; nitriles solvents such as acetonitrile or propionitrile; polar aprotic solvents such as N,N-dimethylformamide or N-methyl pyrrolidone; or the like. The reaction may also be carried out in the absence of a solvent, when an excess of 2-haloethanol is used. In an embodiment, the reaction is carried out in the presence water.

The reaction may be carried out at temperatures ranging from about 25° C. to about 95° C., or from about 70° C. to about 85° C. After the completion of the reaction, the compound of formula (III) may be isolated and optionally purified. In an embodiment, the reaction mass is extracted with dichloromethane, concentrated under vacuum to a minimum volume, co-distilled with another solvent, for example ethyl acetate, and cooled to obtain the compound of formula (III) as solid. The solid thus obtained may be optionally slurried in water, collected by filtration, and dried to yield compound of formula (III) having purity greater than 95%. In one embodiment the purity is greater than 97% by HPLC.

In a particular embodiment, the compound of formula (II) is reacted with 2-chloroethanol in the presence of triethylamine and water, to give a compound of formula (III). In a particular embodiment, R is isopropyl group. In another particular embodiment, the compound of formula (II) is reacted with 2-chloroethanol in the presence of diisopropylethylamine and water, to give a compound of formula (III).

Step b) involves reacting the compound of formula (III) with a chlorinating agent, to give a compound of formula (IV). Chlorinating agents that may be used include, but are not limited to: sulfur-based chlorinating agents such as sulfuryl chloride, thionyl chloride, or the like; and phosphorous-based chlorinating agents such as phosphorous trichloride, phosphorous pentachloride, phosphorous oxychloride, or the like. The amounts of chlorinating agent that may be used range from about 1 to about 6 molar equivalents, per molar equivalent of the compound of formula (III). In particular embodiments, from about 2 to about 4 molar equivalents of thionyl chloride, per molar equivalent of formula (III), are used.

The process may be carried out in the presence a solvent, such as a halogenated hydrocarbon, e.g., 1,2-dichloroethane, dichloromethane, chloroform, or the like. The reaction may be carried out at temperatures ranging from about 0° C. to about 40° C., or from about 25° C. to about 35° C. In a particular embodiment, the compound of the formula (III) is reacted with thionyl chloride in the presence of dichloromethane, to give a compound of formula (IV).

After the completion of the reaction, the compound of formula (IV) may be isolated and optionally purified. In an embodiment, water is added to the reaction mass after completion of the reaction, the layers are separated, the organic layer optionally is concentrated to a minimum volume, and the solid compound of formula (IV) is precipitated by the addition of an anti-solvent. Suitable anti-solvents include, but are not limited to, $C_5$-$C_8$ alkanes such as pentane, hexane, heptane, or the like.

Known processes for the preparation of bendamustine hydrochloride more often do not involve isolation of the compound of formula (IV), and involve direct in situ conversion or involve the conversion of the concentrated reaction mass obtained by distillation to bendamustine hydrochloride. This may result in carrying forward the process impurities, thereby decreasing the yield and purity of the final product. Further, processes involving dry distillation are difficult during scale-up.

Therefore, isolating the compound of formula (IV) as a solid and its optional purification are features of embodiments of the present application. The process for isolating the compound of formula (IV) as disclosed in the present application results in improved color, yield, and purity of the product.

Step c) involves hydrolyzing the compound of formula (IV) to give bendamustine hydrochloride. The hydrolysis of the compound of formula (IV) may be carried out using an acid, such as a mild acid, to give bendamustine hydrochloride. The acids that may be used include mineral acids such as aqueous hydrochloric acid, aqueous sulfuric acid, aqueous phosphoric acid, aqueous perchloric acid, aqueous hydrobromic acid, or carriers containing an acid such as acidic resins. In an embodiment, an acid that may be used in the above step includes aqueous hydrochloric acid having concentrations from about 0.5N to about 5N. The reaction may be carried out at temperatures ranging from about 0° C. to about 60° C., or from about 35° C. to about 50° C. After completion of the reaction, bendamustine hydrochloride may be isolated according to known processes, or by processes as disclosed in the present application.

Another aspect of the present application provides a compound of the formula (IIIa):

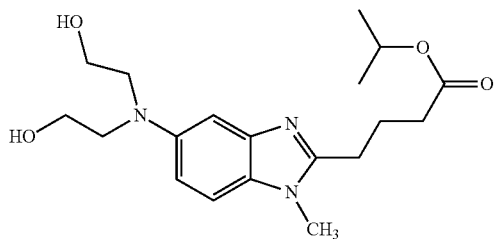

(IIIa)

which is useful as an intermediate for the preparation of bendamustine and its salts.

In an aspect, the present application provides processes for the preparation of bendamustine hydrochloride, embodiments comprising:
a) reacting a compound of formula (IIa):

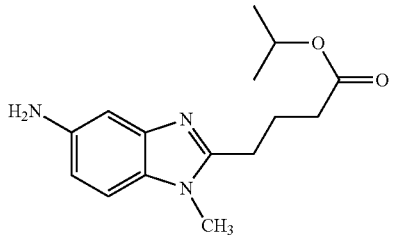

(IIa)

with a 2-haloethanol in the presence of an organic base to give a compound of formula (IIIa);

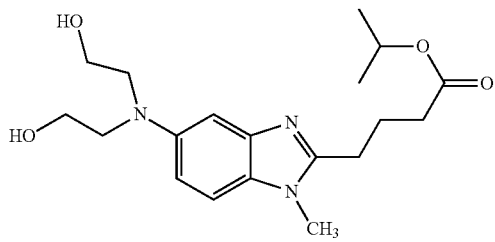

(IIIa)

b) reacting the compound of formula (IIIa) with thionyl chloride in the presence of dichloromethane, to give a compound of formula (IVa); and

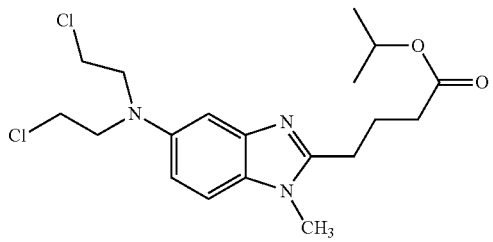

(IVa)

c) hydrolyzing the compound of formula (IVa) using aqueous hydrochloric acid at temperatures less than about 60° C., to give bendamustine hydrochloride.

Use of the compound of the formula (IIIa) or (IVa) as an intermediate and the processes of the present application has the following advantages, as compared to the known processes which involve the use of a corresponding ethyl ester (formula (III) and (IV) where R is ethyl):

Overcomes the problems of isolation of the compound of the formula (III) and (IV) as solids, as compared to various process known in art which used the corresponding ethyl ester (where R is ethyl in compounds of formula (III) and (IV)) resulting in gummy or oily mass.

Isolation as the intermediate compounds of formulae (IIIa) or (IVa) as solids facilitate their purification thereby resulting in improved purity and description of bendamustine hydrochloride.

Requires milder conditions, and temperatures less than 60° C., for the hydrolysis of the compound of formula (Iva), thereby resulting in reduced or substantially no formation of the known impurities HP1 and HP2 as compared to the use of corresponding ethyl ester (where R is ethyl in formula (IV)) which require concentrated hydrochloric acid and reflux temperatures for the hydrolysis, resulting in increased levels of HP1 and HP2.

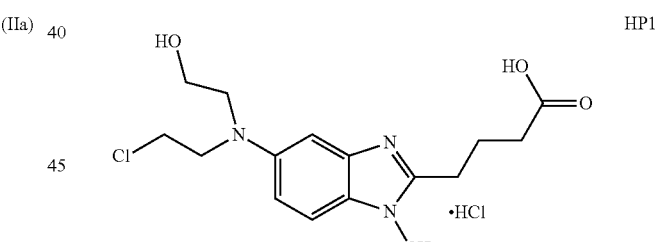

HP1

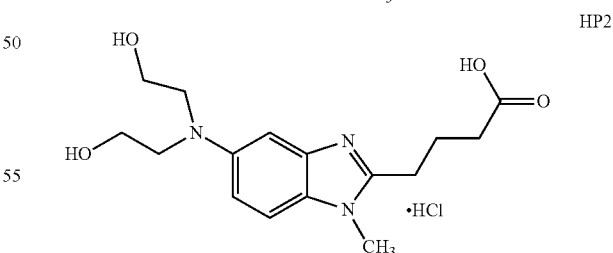

HP2

Another aspect of the present application provides process for the purification of bendamustine hydrochloride, embodiments comprising:
a) providing a suspension of bendamustine hydrochloride in aqueous hydrochloric acid and acetonitrile;
b) heating the suspension of step a) to a temperature of about 35° C. to about 65° C.;

c) cooling the mixture of step b) to a temperature of about 0° C. to about 35° C.;

d) isolating bendamustine hydrochloride.

Steps for this process are separately described below.

Step a) involves providing a suspension of bendamustine hydrochloride in aqueous hydrochloric acid and acetonitrile. The suspension of bendamustine hydrochloride may be provided by combining bendamustine hydrochloride with aqueous hydrochloric acid and acetonitrile or may be obtained from a reaction step by which it is prepared. In an embodiment, a suspension of bendamustine hydrochloride may be provided by combining bendamustine hydrochloride with aqueous hydrochloric acid having concentrations from about 0.1N to about 5N and acetonitrile. In a particular embodiment, about 1.5N aqueous hydrochloric acid is used.

Step b) involves heating the suspension of step a) to a temperature of about 35° C. to about 65° C. The suspension obtained in step a) is heated to a temperature of about 35° C. to about 65° C. to ensure the complete dissolution. In an embodiment, the reaction mixture of step a) is heated to a temperature up to about 50° C. to about 55° C. Optionally, decolonization may be carried out by adding carbon to the solution obtained, maintaining the solution at the same temperature for about 10 minutes to about 2 hours, and filtering the reaction mixture through a Celite® bed.

Step c) involves cooling the mixture of step b) to a temperature of about 0° C. to about 35° C. The solution of bendamustine hydrochloride obtained in step b) may be cooled to a temperature of about 0° C. to about 35° C. and maintained for sufficient time to ensure complete precipitation of the product. In an embodiment, the solution may be cooled to a temperature of from about 25° C. to about 30° C.

d) isolating bendamustine hydrochloride. Isolation of the bendamustine hydrochloride obtained in step c) can be done by techniques known in art which include, but are not limited to filtration by gravity or by suction, distillation, centrifugation, or slow evaporation or the like. The wet product obtained may be dried at a temperature less than about 50° C. In one embodiment, the wet product obtained may be dried at a temperature at a temperature of from about 25° C. to about 35° C. to obtain bendamustine hydrochloride.

The inventors of the present application have found that use acetonitrile along with aqueous hydrochloric acid as the solvent system facilitates the dissolution of bendamustine hydrochloride at lower temperatures and results in products of higher purity levels with reduced levels of the degradation products HP1 and HP2.

The known process for the crystallization of bendamustine hydrochloride uses water alone as the solvent for the crystallization. As the solubility of bendamustine hydrochloride in water is low, which may require maintenance at reflux temperatures, the levels of the HP1 and HP2 impurities in the reaction mass was found to be higher and the product obtained had a slightly higher content of the HP1 impurity. Further, maintenance of the reaction mixture containing water at reflux temperature is not preferable for an industrial scale process.

Crystalline forms are characterized by scattering techniques, e.g., x-ray diffraction powder pattern, by spectroscopic methods, e.g., infra-red, $^{13}C$ nuclear magnetic resonance spectroscopy, and by thermal techniques, e.g., differential scanning calorimetry or differential thermal analysis. The compound of this application is best characterized by the X-ray powder diffraction pattern determined in accordance with procedures that are known in the art. For a discussion of these techniques see J. Haleblain, *J. Pharm. Sci.* 1975 64: 1269-1288, and J. Haleblain and W. McCrone, *J. Pharm. Sci.* 1969 58: 911-929.

In an aspect, the processes of the present application provide bendamustine hydrochloride having a purity greater than about 99.8%. In an embodiment, the processes of the present application provides bendamustine hydrochloride having a purity greater than about 99.9% as determined using HPLC.

In another aspect, the present application provides bendamustine hydrochloride having purity greater than about 99.9% and less than about 0.1% of HP1 and less than about 0.1% of HP2 as determined using HPLC.

In another aspect, the present application provides bendamustine hydrochloride having purity greater than about 99.9%, less than about 0.1% of the compound of formula (IVa), less than about 0.1% of impurity A, and less than about 0.1% of impurity B.

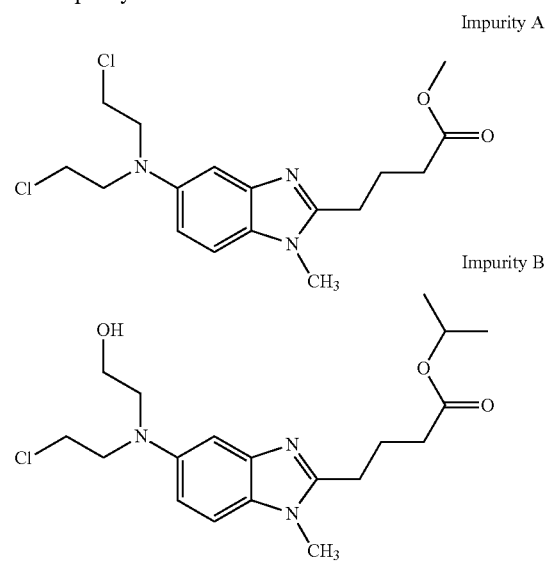

Figure 3:
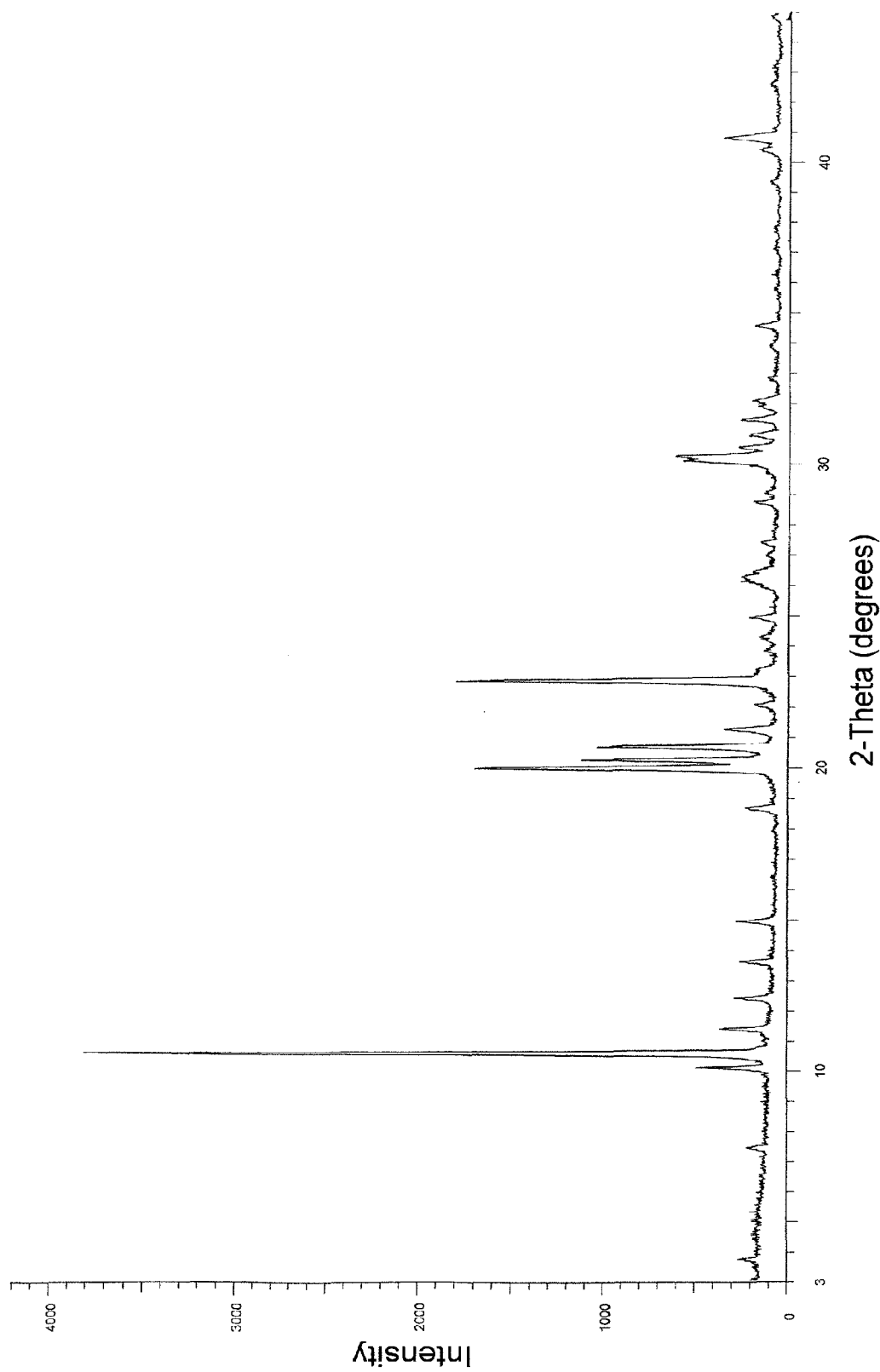
FIG. 3 is an illustrative X-ray powder diffraction pattern of Bendamustine hydrochloride prepared as per Example 6.

In another aspect, the present application provides bendamustine hydrochloride characterized by XRPD pattern substantially as represented in FIG. 3.

In yet another aspect, the present application provides bendamustine hydrochloride characterized by XRPD pattern substantially as represented in FIG. 3, having purity greater than about 99.9% and with less than about 0.1% of HP1 and with less than about 0.1% of HP2 as determined using HPLC.

In an embodiment, the present application provides bendamustine hydrochloride having purity greater than about 99.9% and with less than about 0.1% of each of the compound given in the table below:

| Code | Structure |
|------|-----------|
| HP1  | 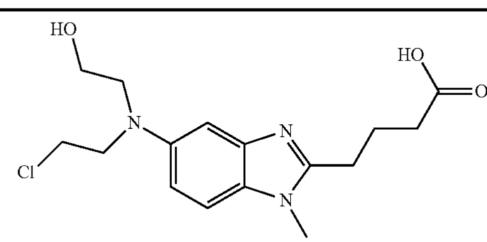          |

| Code | Structure |
|---|---|
| HP2 | (structure) |
| Impurity A | (structure) |
| Impurity B' | (structure) |
| Formula IV | (structure) | wherein R is C₁-C₄alkyl.

The purity of bendamustine hydrochloride and its related substances or impurities may be analyzed using various methods. A representative useful HPLC method is described below.

Column: Inertsil ODS 2, (150×4.6) mm, 5 μm
Column temperature: 27±2° C.
Sample cooling rack temperature: 5° C.
Injection volume: 10 μL
Elution: Gradient
Run time: 60 minutes
Mobile Phase A: Dissolve 1.0 ml of trifluoroacetic acid in 1000 ml of water, mix and degas.
Mobile Phase B: Acetonitrile
Flow rate: 1.0 mL/min.
Wavelength of detection: 233 nm UV.
Diluent: Buffer: dissolve 1.36 gm of potassium dihydrogen orthophosphate in 1000 ml of Milli Q™ Water and adjust the pH to 1.9 with dilute hydrochloric acid.
Mix and degas buffer and Acetonitrile in the ratio of 7:3 v/v.
Sample Concentration: 0.6 mg/ml Gradient program:

| Minutes | % Mobile Phase A | % Mobile Phase B |
|---|---|---|
| 0 | 95 | 5 |
| 5 | 90 | 10 |
| 20 | 70 | 30 |
| 30 | 60 | 40 |
| 40 | 40 | 60 |
| 45 | 30 | 70 |
| 50 | 50 | 50 |
| 55 | 95 | 5 |
| 60 | 95 | 5 |

The X-ray powder diffraction patterns described herein were generated using a Bruker AXS D8 Advance powder X-ray diffractometer, with a copper $K_\alpha$ radiation source (1.5418 Å). Generally, a diffraction angle (2θ) in powder X-ray diffractometry may have a permissible variation in the range of ±0.2°. Therefore, the aforementioned diffraction angle values should be understood as including values in the range of about ±0.2°. Accordingly, the present disclosure includes not only crystals whose peak diffraction angles in powder X-ray diffractometry completely coincide with each other, but also crystals whose peak diffraction angles coincide with each other with a permissible variation of about ±0.2°. Although the intensities of peaks in the x-ray powder diffraction patterns of different batches of a compound may vary slightly, the peaks and the peak locations are characteristic for a specific polymorphic form. The relative intensities of the PXRD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of PXRD is meant to encompass that peak assignments can vary by plus or minus about 0.2°. Moreover, new peaks may be observed or existing peaks may disappear, depending on the type of the machine or the settings (for example, whether a Ni filter is used or not).

DEFINITIONS

The following definitions are used in connection with the present application unless the context indicates otherwise. Celite® is flux-calcined diatomaceous earth. Celite® is a registered trademark of World Minerals Inc. DARCO® is a registered trademark of Norit Americas Inc. Marshall, Tex. "Halo" or "halogen" refers to fluorine, chlorine, bromine, or iodine, HPLC means High Pressure Liquid Chromatography. Polymorphs are different solids sharing the same molecular formula, yet having distinct physical properties when compared to other polymorphs of the same formula. The term "reacting" is intended to represent bringing together the chemical reactants under conditions such to cause the chemical reaction indicated to take place.

"About" means within an acceptable standard variation of the mean, when considered by one of ordinary skill in the art.

An "alkane solvent" refers to a liquid, saturated hydrocarbon, which may be linear or branched. It is capable of dissolving a solute to form a uniformly dispersed solution. Examples of a $C_5$-$C_8$alkane solvent include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, $C_5$-$C_8$aliphatic hydrocarbons, and mixtures thereof.

"Alkyl-" refers to a hydrocarbon chain that may be a straight chain or branched chain, containing the indicated number of carbon atoms, for example, a $C_1$-$C_{10}$alkyl-group may have from 1 to 10 (inclusive) carbon atoms in it. In the absence of any numerical designation, "alkyl" is a chain (straight or branched) having 1 to 6 (inclusive) carbon atoms in it. Examples of $C_1$-$C_4$alkyl-groups include, but are not limited to, methyl, ethyl, propyl, butyl, isopropyl, isobutyl, sec-butyl, and tert-butyl. Examples of $C_5$-$C_8$alkyl-groups include, but are not limited to, pentyl, hexyl, heptyl, isopentyl, neopentyl, and isohexyl.

"Chlorinating agent" refers to various inorganic and organic reagents having the functionality of an acid chloride. Examples of a chlorinating agent include, but are not limited to, antimony trichloride, n-chlorosuccinimide, ferric chloride, nitryl chloride, oxalyl chloride, phosphorus oxychloride, phosphorus pentachloride, phosphorus trichloride, sulfur dichloride, sulfuryl chloride, phosgene; oxalyl chloride, chloromethylenedimethylammonium chloride, dry HCL gas, and thionyl chloride.

A "halogenated hydrocarbon solvent" is an organic solvent containing a carbon bound to a halogen. "Halogenated hydrocarbon solvents" include, but are not limited to, dichloromethane, 1,2-dichloroethane, trichloroethylene, perchloroethylene, 1,1,1-trichloroethane, 1,1,2-trichloroethane, chloroform, carbon tetrachloride, or the like.

An "inorganic base" is an inorganic compound, which acts as a base. Examples of such bases include, but are not limited to, hydrides, hydroxides, carbonates, bicarbonates, oxides, carboxylates, and alkoxides of alkali or alkaline earth metals, such as lithium hydride, sodium hydride, potassium hydride, lithium hydroxide, sodium hydroxide, potassium hydroxide, lithium carbonate, sodium carbonate, potassium carbonate, calcium carbonate, cesium carbonate, calcium oxide, and barium oxide or ammonium hydroxide.

An "organic base" is an organic compound, which acts as a base. Examples of such bases include, but are not limited to, triethylamine, diisopropylamine, Hunig's base, DABCO, triethanolamine, tributyl amine, pyridine, lutidine, 4-dimethylaminopyridine (DMAP), diethanolamine, 4-methylmorpholine, dimethylethanolamine, tetramethyl guanidine, tetramethylammonium hydroxide, tetraethylammonium hydroxide, N-methyl-1,5,9-triazabicyclo[4.4.0]decene, 1,8-diazabicyclo[5.4.0]undec-7-ene, dicyclohexyl amine, and picoline.

A "nitrile solvent" is an organic solvent containing a cyano —(C≡N) bonded to another carbon atom. "Nitrile solvents" include, but are not limited to, acetonitrile, propionitrile, $C_{2-6}$nitriles, or the like.

A "polar aprotic solvent" has a dielectric constant greater than 15 and is at least one selected from the group consisting of amide-based organic solvents, such as hexamethyl phosphoramide (HMPA), and hexamethyl phosphorus triamide (HMPT); nitro-based organic solvents, such as nitromethane, nitroethane, nitropropane, and nitrobenzene; ester-based organic solvents, such as γ-butyrolactone, ethylene carbonate, propylene carbonate, butylene carbonate, dimethyl carbonate, and propiolactone; pyridine-based organic solvents, such as pyridine and picoline; and sulfone-based solvents, such as dimethyl sulfone, diethyl sulfone, diisopropylsulfone, 2-methylsulfolane, 3-methylsulfolane, 2,4-dimethylsulfolane, 3,4-dimethyl sulfolane, 3-sulfolene, and sulfolane. These organic solvents may be used alone or two or more of these may be combined appropriately.

Certain specific aspects and embodiments of the present application will be explained in greater detail with reference to the following examples, which are provided only for purposes of illustration and should not be construed as limiting the scope of the application in any manner.

EXAMPLES

Example 1

Preparation of 4-{5[bis-(2-hydroxyethyl)amino]-1-methyl, 1H-benzoimidazol-2-yl}-butyric acid isopropyl ester 4-(5-Amino-1-methyl-1H-benzoimidazol-2-yl)-butyric acid isopropyl ester (15.0 g), water (30 mL), 2-chloroethanol (15.6 mL, 4.0 M) and triethyl amine (22.7 mL 3.0 M), are charged into a round bottom flask and stirred. The reaction mixture is heated to about 70-75° C. and maintained for about 2 hours. 2-Chloroethanol (7.8 mL, 2.0 M) and triethylamine (22.7 mL, 3.0 M) are added to the reaction mixture and stirred at the same temperature for about 90 minutes. 2-Chloroethanol (7.8 mL, 2.0 M) and triethylamine (22.7 mL, 3.0 M) are added to the reaction mixture and stirred at the same temperature for about 2 hours. 2-Chloroethanol (7.8 mL, 2.0 M) is added to the reaction mixture and stirred at the same temperature for about 4 hours. Triethylamine (11.3 mL, 1.5 M) is added to the reaction mixture and maintained at the same temperature for about 4 hours. The reaction mixture is cooled to 25-30° C., then dematerialized water (300 mL) is added and stirred. The reaction mass is extracted with dichloromethane (3×150 mL). The obtained dichloromethane extract is washed with saturated sodium bicarbonate solution (150 mL), followed by saturated sodium chloride (150 mL), and dried over sodium sulfate. The dichloromethane layer is concentrated under vacuum at about 40-45° C. to give a residue, which is dissolved in ethyl acetate (75 mL) and concentrated at 40-45° C. under vacuum to give a viscous mass. The obtained mass is dissolved in ethyl acetate (45 mL), then n-hexane (225 mL) is added slowly at 27° C. and stirred for 1 hour. The obtained solid is collected by filtration, washed, and dried in a vacuum oven at 45-50° C. for about 4-5 hours, to give the title compound. Yield: 13.0 g (68%).

4-{5-[Bis-(2-hydroxyethyl)amino]-1-methyl,1H-benzoimidazol-2-yl}-butyric acid isopropyl ester (5 g) and acetonitrile (8 mL) are charged into a round bottom flask and heated to 60-65° C. The mass is maintained at the same temperature for about 15 minutes, cooled to 25-30° C., stirred for about 1 hour, filtered, and the collected solid is washed with chilled acetonitrile (5 mL). The solid is dried under vacuum at 48° C. for about 4 hours to give the title compound. Yield: 3.6 g (72%).

Example 2

Preparation of 4-{5-[bis-(2-chloroethyl)amino]-1-methyl 1H-benzoimidazol-2-yl}-butyric acid isopropyl ester 4-{5-[Bis-(2-hydroxyethyl)amino]-1-methyl-1H-benzimidazol-2-yl}-butyric acid isopropyl ester (5 g) and dichloromethane (75 mL) are charged into a round bottom flask and cooled to 0-5° C. Thionyl chloride (4 mL, 4.0 M) is slowly added at the same temperature. The temperature is allowed to rise to 25-30° C. and the mixture is stirred for about 7 hours. Water (100 mL) is slowly added and the mixture is stirred for about 20 minutes, then the layers are separated. The dichloromethane layer is washed with saturated sodium bicarbonate solution (100 mL), dried over sodium sulfate, and is concentrated under vacuum at 30-33° C. to obtain 10-15 mL of a concentrated mass. n-Heptane (100 mL) is added to the concentrated mass slowly at 27° C., stirred for about 1 hour, filtered, and the collected solid is washed with n-heptane (15 mL) and dried under vacuum to give the title compound. Yield: 3.4 g (61%).

Example 3

Preparation of Bendamustine Hydrochloride

4-{5-[Bis-(2-chloroethyl)amino]-1-methyl-1H-benzimidazol-2-yl}-butyric acid isopropyl ester (3 g) is charged into a round bottom flask and 50% hydrochloric acid solution (21 mL) is slowly added. The mixture is heated to 35-40° C., maintained for about 90 minutes, and concentrated under vacuum at about 55-58° C., to give a viscous mass. Warm water (12 mL, 55-60° C.) is added and the mixture is stirred for about 1 hour. The obtained solid is collected by filtration, washed with water (3 mL), and dried under vacuum at 45-50° C. for 4 hours to give bendamustine hydrochloride. Yield: 2.2 g (75%).

Example 4

Purification of Bendamustine Hydrochloride

Bendamustine hydrochloride (3 g, purity: 98.23%), aqueous hydrochloride (obtained from 4.05 mL concentrated hydrochloric acid and 22.95 mL water) and acetonitrile (3 mL) are charged into a round bottom flask. The mixture is heated to 50-55° C. and maintained for about 2 hours. Carbon (300 mg) is charged to the mixture, maintained for 10 minutes, filtered through the Celite® bed and washed with water (3 mL). The filtrate obtained is transferred to another round bottom flask, cooled to 25-30° C., and maintained for 60 minutes. The solid obtained is collected by filtration, washed with water (15 mL), and dried under vacuum at 25-30° C. for 2 hours to give bendamustine hydrochloride. Yield: 1.84 g (61.35%). Purity: 99.90%; HP1: 0.07%, HP2: Not detected; Formula (Iva): 0.02%; Impurity A: Not detected, Impurity B: Not detected.

Example 5

Preparation of Bendamustine Hydrochloride by Crystallization from Water

Bendamustine hydrochloride (4 g) and water (52 mL) are charged into a round bottom flask. The mixture is heated to 60° C. to obtain a clear solution and maintained for 10 minutes. Cooled the reaction mixture to 25-30° C. and maintained for 2 hours 15 minutes. The solid obtained is collected by filtration, washed with water (4 mL), dried by suction for 15 minutes, and divided into two equal parts.

PART-A: The first part of the wet compound was dried under vacuum at 35° C. for about 1 hour to give bendamustine hydrochloride. Yield: 1.2 g, XRPD pattern: FIG. 1.

Figure 2:
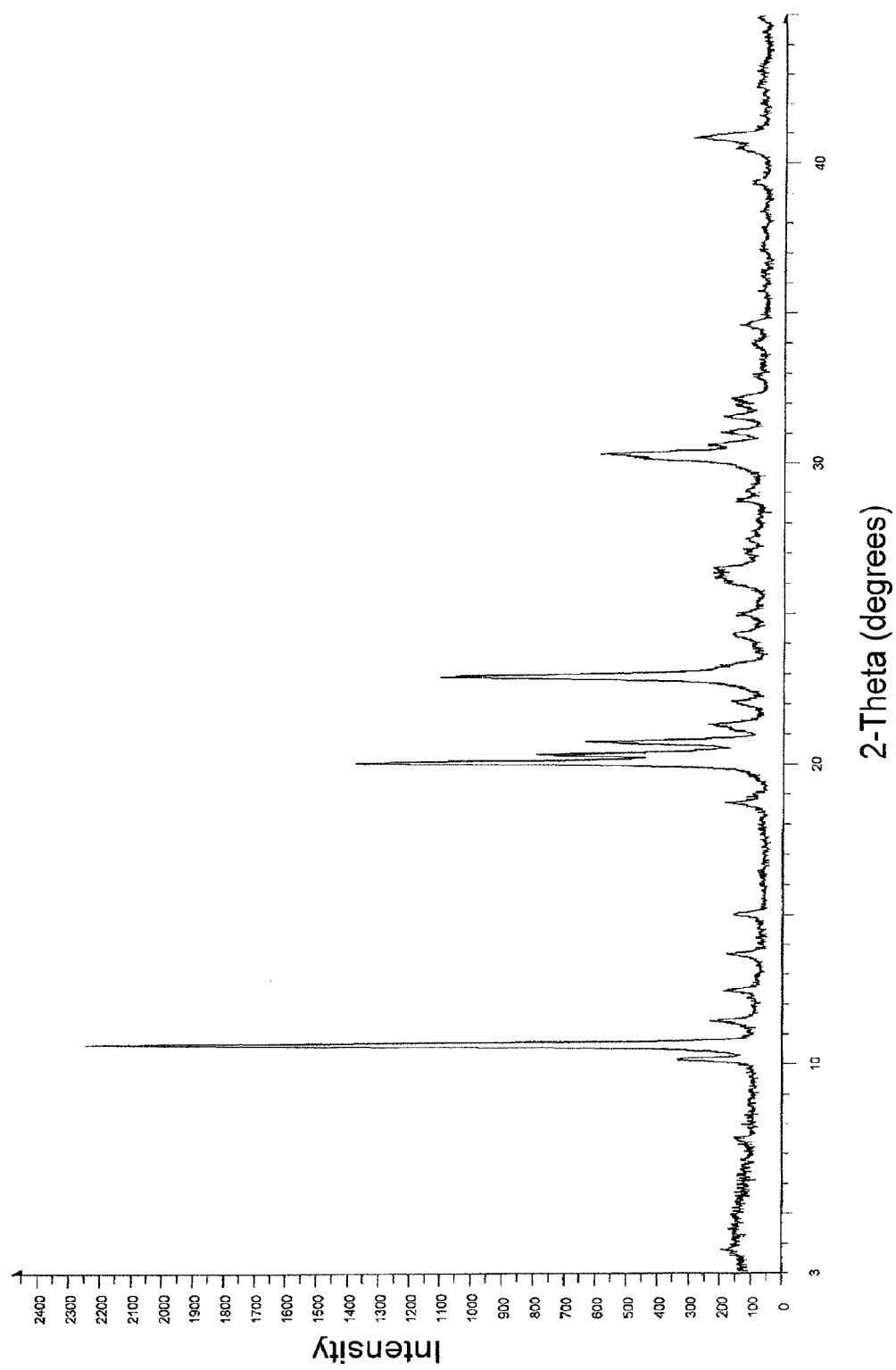
FIG. 2 is an illustrative X-ray powder diffraction pattern of Bendamustine hydrochloride prepared as per Example 5 (Part-B).

PART-B: The second part of the wet compound was dried under vacuum at 45° C. for about 1 hour to give bendamustine hydrochloride. Yield: 1.0 g, XRPD pattern: FIG. 2.

Example 6

Preparation of Bendamustine Hydrochloride by Crystallization from Aqueous Hydrochloric Acid and Acetonitrile Bendamustine hydrochloride (55 g), a mixture of acetonitrile and aqueous hydrochloride (550 mL; obtained from 74.25 mL concentrated hydrochloric acid, 420.75 mL water and 55 mL acetonitrile) are charged into a round bottom flask. The mixture is heated to 50-55° C. and maintained for 35 minutes. Darco® G80 (5.5 g) is charged to the mixture, maintained for 10 minutes, filtered through the Celite® bed and washed with water (55 mL). The filtrate obtained is transferred to another round bottom flask, cooled to 25-30° C., and maintained for 75 minutes. The solid obtained is collected by filtration, washed with water (55 mL), and dried under vacuum at 29° C. to give bendamustine hydrochloride. Yield: 34 g (62%), Purity: 99.89%, XRPD pattern: FIG. 3; Moisture content: 4.84%.

Example 7

Preparation of 4-{5[bis-(2-hydroxyethyl)amino]-1-methyl, 1H-benzoimidazol-2-yl}-butyric acid isopropyl ester using potassium carbonate as the base 4-(5-Amino-1-methyl-1H-benzoimidazol-2-yl)-butyric acid isopropyl ester (4.25 g), 2-chloroethanol (15.6 mL, 15 M), and potassium carbonate (2.13 g, 1.0 M), are charged into a round bottom flask and stirred. The reaction mixture is heated to about 80° C. and maintained for about 9 hours. The reaction mixture is cooled to 25-30° C., slowly added water (425 mL), the pH of the reaction mass is adjusted to pH 5-6 using 3N hydrochloric acid, and the reaction mass is extracted with dichloromethane (2×200 mL). Adjusted the pH of the reaction mass to pH 8-9 using saturated sodium bicarbonate solution and extracted with dichloromethane (3×200 mL). Combined the dichloromethane extracts and concentrated completely under vacuum. Yield: 10.6 g, Purity by HPLC: 73.5%; Impurity C: 16.32%.

Example 8

Preparation of 4-{5-[bis-(2-hydroxyethyl)amino]-1-methyl, 1H-benzo-imidazol-2-yl}-butyric acid isopropyl ester using diisopropyl ethylamine as the base 4-(5-Amino-1-methyl-1H-benzoimidazol-2-yl)-butyric acid isopropyl ester (400 g), water (800 mL), 2-chloroethanol (390.8 mL, 4.0 M), and diisopropyl ethylamine (761.2 mL 3.0 M), are charged into a round bottom flask and stirred. The reaction mixture is heated to about 85-90° C. and maintained for about 6 hours. The reaction mixture is cooled to 25-30° C. and extracted with dichloromethane (2000 mL, 1000 mL, and 1000 mL). The dichloromethane extract are combined, washed with saturated sodium chloride solution (2×1200 mL), and concentrated under vacuum at about 47° C. to obtain 1200 mL of the concentrated mass of dichloromethane extracts. The obtained mass is washed with water (3600 mL) and concentrated under vacuum at about 47° C. to obtain 400 mL of the concentrated mass. Ethyl acetate (1200 mL) is added to the mass and concentrated at about 47° C. under vacuum to give a viscous mass. The obtained mass is dissolved in ethyl acetate (600 mL), cooled to 0-5° C., and maintained at the same temperature for about 1 hour. The obtained solid is filtered, washed with cold ethylacetate and suction dried.

Charged the obtained solid and water (2400 mL) into a round bottom flask and stirred at 28° c. for 2 hours. Collected the solid by filtration, washed with water (800 mL), and dried under vacuum at 50° C. for 5 hours. Yield: 235.0 g, Purity by HPLC: 97.60%, Impurity C: not detected.

Example 9

Preparation of Bendamustine Hydrochloride

4-{5-[Bis-(2-hydroxyethyl)amino]-1-methyl-1H-benzimidazol-2-yl}-butyric acid isopropyl ester (5 g) and dichloromethane (50 mL) are charged into a round bottom flask and stirred at 28° C. Thionyl chloride (2.6 mL, 2.6 M) is slowly added at the same temperature and the reaction mass is allowed to settle for 30 minutes. The reaction mixture is heated to a temperature of 38-40° C. and the mixture is stirred for 90 minutes. Cooled the reaction mass to 25-30° C., dichloromethane layer (25 mL) and water (25 mL) are added and stirred. Separated the organic layer and washed with saturated sodium bicarbonate solution (25 mL) and saturated brine solution (25 mL). The organic layer is concentrated under vacuum at 45° C. to obtain 10-15 mL of the concentrated mass, cooled the mass to 25-30° C. N-heptane (62.5 mL) is added to the mass slowly at 28° C., stirred for about 1 hour, filtered and dried under vacuum to give 4-{5-[bis-(2-chloroethyl)amino]-1-methyl 1H-benzoimidazol-2-yl}-butyric acid isopropyl ester compound. Yield: 4.4 g.

4-{5-[Bis-(2-chloroethyl)amino]-1-methyl-1H-benzimidazol-2-yl}-butyric acid isopropyl ester (4 g), is added to a mixture of water (13.6 mL) and concentrated hydrochloric acid (5.4 mL) in a round bottom flask. The mixture is heated to 40-45° C., maintained for 8 hours. Cooled the reaction mass to 25-30° C., stirred for 90 minutes, filtered, washed with water (12 mL), and dried under vacuum of 500-600 mm of Hg at 29° C. for 3 hours to give bendamustine hydrochloride. Yield: 2.7 g (75%).

Example 10

Purification of Bendamustine Hydrochloride

Bendamustine hydrochloride (5 g) is added to a mixture of acetonitrile and aqueous hydrochloride (obtained from 6.75 mL concentrated hydrochloric acid, 38.25 mL water and 5.0 mL acetonitrile) in a round bottom flask. The mixture is heated to 50-55° C. and maintained for about 90 minutes. Darco® (1.5 g) is charged to the mixture, maintained for 30 minutes, filtered through the Celite® bed and washed with water (5 mL). The filtrate obtained is transferred to another round bottom flask, cooled to 25-30° C., and maintained for 90 minutes. The solid obtained is collected by filtration, washed with water (5 mL), and dried under vacuum of 500-600 mm of Hg at 25-30° C. for 3 hours to give bendamustine hydrochloride. Yield: 3.25 g (65%). Purity: 99.80%; HP1: 0.04%, HP2: not detected; Formula (Iva): 0.04%; Impurity A: 0.02%, Impurity B: not detected.

Throughout this application, various publications are referenced. The disclosures of these publications in their entireties are hereby incorporated by reference into this application in order to more fully describe the state of the art as known to those skilled therein as of the date of the application described and claimed herein.

While particular embodiments of the present application have been illustrated and described, it would be obvious to those skilled in the art that various other changes and modifications can be made without departing from the spirit and scope of the application. It is therefore intended to cover in the appended claims all such changes and modifications that are within the scope of this invention.

The invention claimed is:

1. A process comprising:
a) reacting a compound of formula (II):

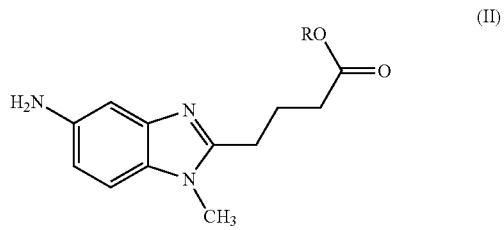

wherein R is a $C_1$-$C_4$ alkyl group, with a 2-haloethanol in the presence of an organic base to give a compound of formula (III);

(III)

b) reacting the compound of formula (III) with a chlorinating agent to provide a compound of formula (IV); and (IV)

c) hydrolyzing the compound of formula (IV) to give bendamustine hydrochloride.

2. The process of claim 1, wherein the 2-haloethanol consists of 2-chloroethanol, 2-bromoethanol, or 2-iodoethanol.

3. The process of claim 1, wherein the organic base consists of triethylamine, diisopropyl amine, diisopropyl-ethylamine, DABCO, pyridine, lutidine, 4-dimethylaminopyridine, or 4-methylmorpholine.

4. The process of claim 1, wherein the organic base consists of triethylamine, diisopropyl amine, or diisopropyl-ethylamine.

5. The process of claim 1, wherein the chlorinating agent used in step b) consists of sulphuryl chloride, thionyl chloride, phosphorous trichloride, phosphorous pentachloride, or phosphorous oxychloride.

6. The process of claim 1, wherein step b) is carried out in the presence of a halogenated hydrocarbon solvent.

7. The process of claim 1, where in step b) consists of:
a) reacting the compound of formula (III) with a chlorinating agent in the presence of a halogenated hydrocarbon solvent;

b) adding water;

c) separating the organic layer, optionally concentrating to a minimum volume;

d) adding an anti-solvent selected from a $C_5$-$C_8$ alkane, such as pentane, hexane, or heptane; and e) isolating the compound of formula (IV) as a solid.

8. The process of claim 1, wherein step c) is carried out using aqueous hydrochloric acid.

9. The process of claim 1, wherein step c) is carried out using aqueous hydrochloric acid having concentration from about 0.5N to about 5N.

10. The process of claim 1, wherein step c) is carried out using aqueous hydrochloric acid and at temperatures less than about 60° C.

11. The process of claim 1, further comprising:

a) purification of the bendamustine hydrochloride, by combining it with aqueous hydrochloric acid, and acetonitrile;

b) heating the mixture of step a) to a temperature from about 35° C. to about 65° C.;

c) cooling the mixture of step b) to a temperature from about 0° C. to about 35° C.; and d) isolating bendamustine hydrochloride.

\* \* \* \* \*